(12) United States Patent
Domack

(10) Patent No.: US 7,597,845 B2
(45) Date of Patent: Oct. 6, 2009

(54) APPARATUS FOR SELECTIVELY HOLDING AND RELEASING AN OBJECT IN AN ANALYSIS SYSTEM

(75) Inventor: Thomas E. Domack, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 807 days.

(21) Appl. No.: 10/923,975

(22) Filed: Aug. 23, 2004

(65) Prior Publication Data

US 2006/0039822 A1 Feb. 23, 2006

(51) Int. Cl.
*G01N 21/00* (2006.01)
(52) U.S. Cl. ...................................................... 422/63
(58) Field of Classification Search .................... 422/63
See application file for complete search history.

(56) References Cited

U.S. PATENT DOCUMENTS

| | | | |
|---|---|---|---|
| 3,734,556 A * | 5/1973 | Misawa | 294/88 |
| 4,780,047 A * | 10/1988 | Holt et al. | 414/730 |
| 4,878,705 A * | 11/1989 | Arnquist | 294/116 |
| 5,209,903 A | 5/1993 | Kanamori et al. | |
| 5,523,662 A * | 6/1996 | Goldenberg et al. | 318/568.11 |
| 5,804,145 A | 9/1998 | Gao et al. | |
| 5,882,596 A | 3/1999 | Breeser et al. | |
| 6,005,462 A * | 12/1999 | Myers | 335/220 |
| 6,145,403 A * | 11/2000 | Aschenbrenner et al. | 74/490.01 |
| 2003/0026732 A1* | 2/2003 | Gordon et al. | 422/63 |
| 2004/0135388 A1* | 7/2004 | Sgobero et al. | 294/100 |

* cited by examiner

*Primary Examiner*—Walter D Griffin
*Assistant Examiner*—Bobby Ramdhanie
(74) *Attorney, Agent, or Firm*—Sterne, Kessler, Goldstein & Fox P.L.L.C.

(57) ABSTRACT

An apparatus for selectively holding and releasing an object in an analysis system is set forth. The apparatus comprises first and second arm assemblies that are mounted for rotation about a corresponding pair of axes. Each arm assembly includes an object holding end and a magnetic end disposed opposite one another about the respective axis. A magnetic drive is provided to magnetically induce rotation of the magnetic ends of the first and second arm assemblies about their respective axes between an open state in which the holding ends are distal one another to allow placement of the object that is to be held therebetween and a closed state in which the holding ends are driven proximate the object. The apparatus may be readily adapted to receive and hold a variety of objects, such as test tubes, vials, microscope slides, etc.

48 Claims, 7 Drawing Sheets

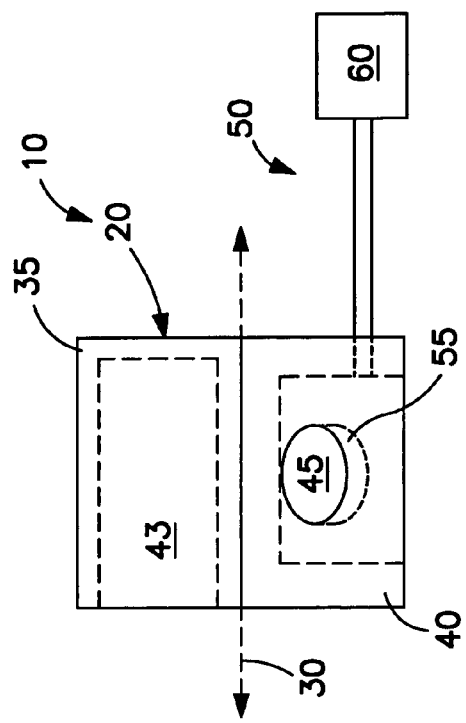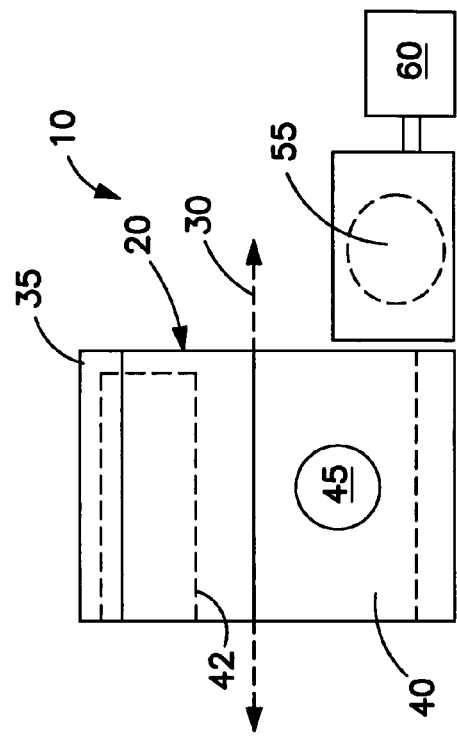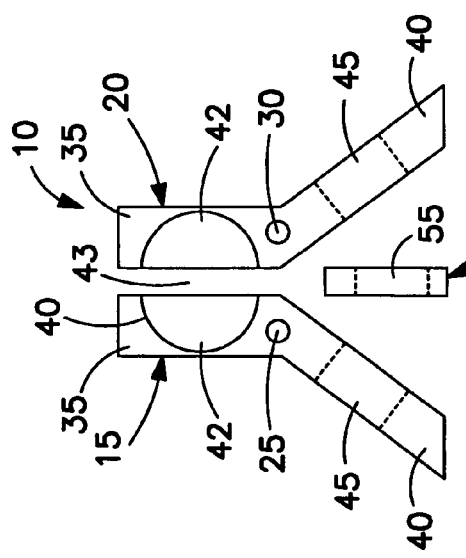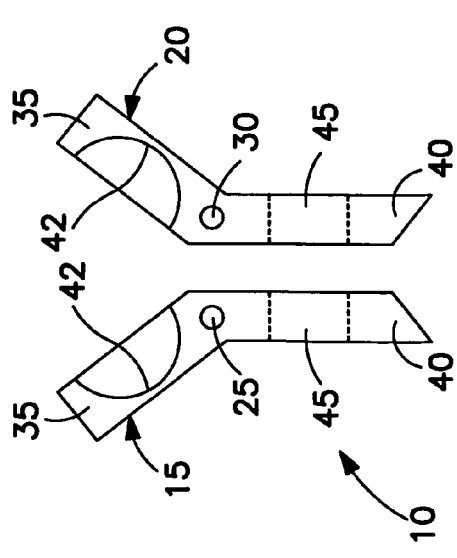

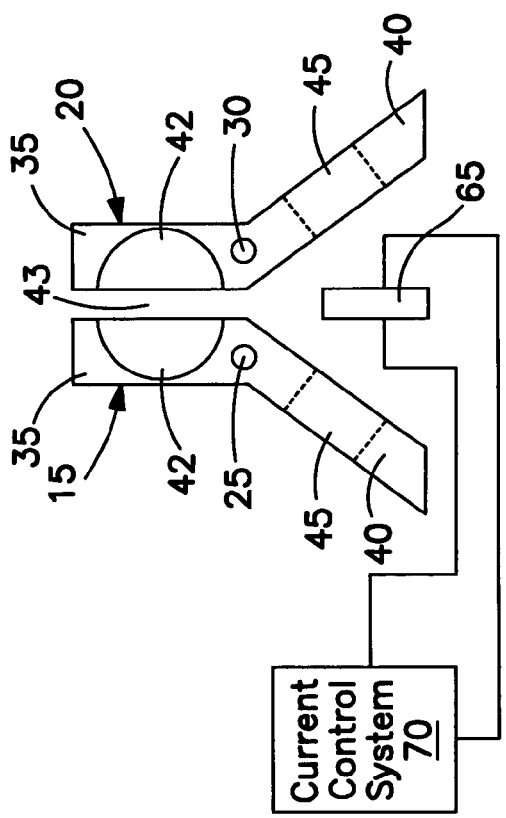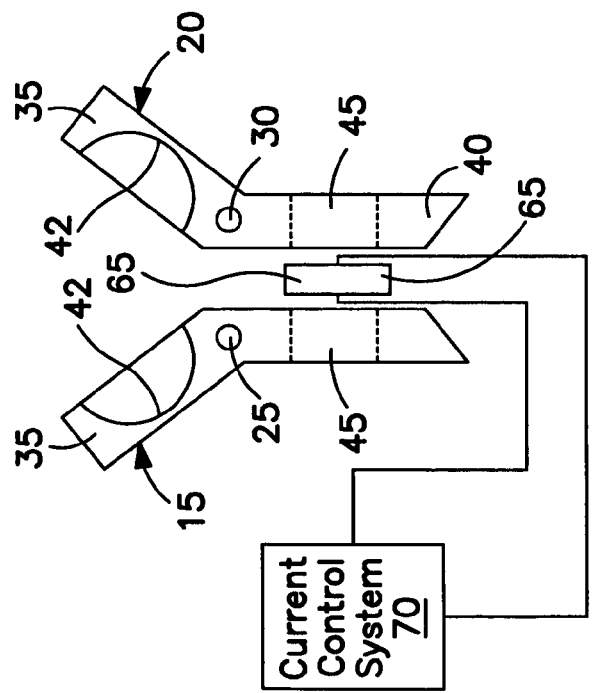

APPARATUS FOR SELECTIVELY HOLDING AND RELEASING AN OBJECT IN AN ANALYSIS SYSTEM

FIELD OF THE INVENTION

The present invention is generally directed to improvements in apparatus used to prepare and analyze the chemical and/or biological properties of a sample. More particularly, the present invention is directed to improvements in apparatus for selectively holding and releasing an object in an analysis system.

BACKGROUND OF THE INVENTION

Apparatus used in the analysis of chemical and/or biological properties of a sample and in sample preparation take on a variety of shapes and forms. Despite their variety, most of these apparatus include common mechanisms that are designed to selectively hold an object, such as a slide, test tube, etc., as the object is transported or otherwise manipulated in the system.

One such apparatus is set forth in U.S. Pat. No. 5,804,145, to Gao et al. The '145 patent is directed to an apparatus for making blood smears on microscope slides. During the blood smearing process, a microscope slide is received and carried by a slide truck. The truck comprises a body portion having a slide-receiving platform as its bottom surface. The platform has a recess formed therein that communicates with a vacuum port. When a vacuum is applied to the port while the platform is closely spaced from a microscope slide, the slide is drawn to and held against the platform by the pressure of the vacuum. The truck, carrying the slide, moves along a predetermined path as blood is smeared across the surface of the slide.

Another apparatus adapted to analyze blood is set forth in U.S. Pat. No. 5,209,903, to Kanamori et al. The '903 patent includes a conveyor for handling and transporting sample blood through a blood analyzer and an automatic blood smear generator that is placed under the control of a programmable controller. In accordance with one aspect of the apparatus, a printer is used to print unique identifiers on each slide. To this end, a printer head of the printer is positioned directly above a slide as the slide is supported on a guide plate. The guide plate steps the slides under the printer one at a time as the identification codes are printed on them. A holder is used to hold the slide during this printing process. The holder comprises a pair of arms that are pivotally attached to a common support. The arms are disposed to rotate toward and away from one another and are driven by a piston that is connected to a pneumatic source. Protrusions that extend from each arm close over opposite edges of the slide to hold the slide securely against the guide plate while the identifying code is printed.

An apparatus for use in an automated chemical analyzer is set forth in U.S. Pat. No. 5,882,596, to Breeser et al. The '596 patent discloses a vessel shuttle that can be used for moving reaction vessels, such as test tubes, to or from an assay resource station in the analyzer. The shuttle has a plurality of movable plates that are adapted to move cooperatively with respect to one another to advance a vessel stepwise along a linear path without a corresponding net motion of the carrying plates during the advancement. Each plate supports a plurality of the vessels in corresponding fixed slots formed in the plate.

The foregoing apparatus use pneumatic drives and/or complex mechanical arrangements to achieve the desired grasping, transport and/or manipulation of the test objects. In apparatus employing pneumatic drives, a separate pneumatic/vacuum system is provided thereby increasing the overall cost and complexity of the apparatus. Similarly, complex mechanical arrangements increase manufacturing costs as well as cost of ownership due to reduced reliability. Accordingly, an apparatus for selectively holding and releasing an object in an analysis system that is less mechanically complex and has simplified drive requirements is desirable in many situations.

SUMMARY OF THE INVENTION

An apparatus for selectively holding and releasing an object in an analysis system is set forth. The apparatus comprises first and second arm assemblies that are mounted for rotation about a corresponding pair of axes. Each arm assembly includes an object holding end and a magnetic end disposed opposite one another about the respective axis. A magnetic drive is provided to magnetically induce rotation of the magnetic ends of the first and second arm assemblies about their respective axes between an open state in which the holding ends are distal one another to allow placement of the object that is to be held therebetween and a closed state in which the holding ends are driven proximate the object. The apparatus may be readily adapted to receive and hold a variety of objects, such as test tubes, vials, microscope slides, etc.

BRIEF DESCRIPTION OF THE DRAWINGS

FIGS. 1A through 1D are schematic views of a first embodiment of the present invention that is adapted to selectively hold and release an object such as a test tube or vial.

FIGS. 2A and 2B are schematic views of a variation on the first embodiment of FIGS. 1A through 1D in which an electromagnet is used to drive the apparatus between the open and closed states.

DESCRIPTION OF A PREFERRED EMBODIMENT OF THE INVENTION

Figure 3D:
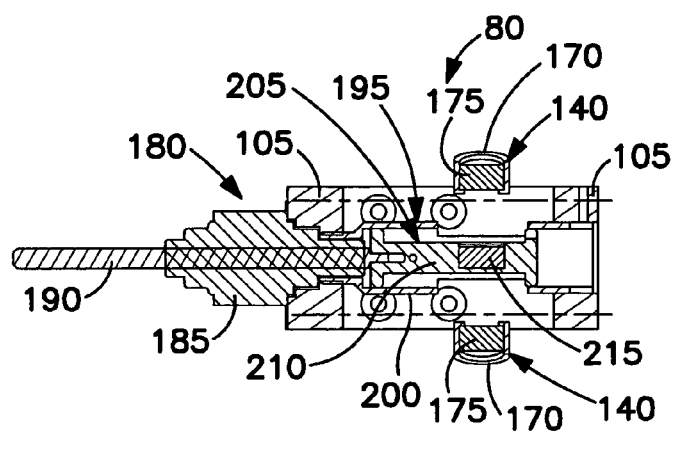
FIGS. 3A through 3E are schematic views of a second embodiment of the present invention that is adapted to selectively hold and release a microscope slide and showing the embodiment in its closed state.

FIGS. 1A through 1D illustrate one embodiment of an apparatus for selectively holding and releasing an object in an analysis system. This particular embodiment of the apparatus, shown generally at 10, is adapted to hold a vessel, such as a vial or test tube. However, it will be recognized that the apparatus may be readily adapted to hold objects of different types as well.

The apparatus 10 includes a first arm assembly 15 and a second arm assembly 20 that are disposed opposite one another. In the illustrated embodiment, the first and second arm assemblies 15 and 20 are formed as mirror images. Each arm assembly 15 and 20 is mounted for rotation about a corresponding rotation axis, shown here as axes 25 and 30, respectively. Axes 25 and 30 are preferably in a spaced apart relationship and generally parallel with one another. Each axis 25 and 30 may be centered on corresponding pivot rods that support each arm assembly 15 and 20.

Generally stated, each arm assembly 15 and 20 includes an object holding end 35 and a magnetic end 40 that are disposed on opposite sides of the corresponding rotation axis. Each object holding end 35 has a generally arcuate opening 40 extending at least partially therethrough. The arcuate openings 42 cooperate with one another to form a vessel holding pocket 43 when the arms 15 and 20 are in the object holding position shown in FIG. 1A. The shape of the vessel holding pocket 43 depends on the exterior shape of the particular type of vessel that is to be held or transported by the apparatus 10.

The magnetic end 40 of each arm assembly 15 includes one or more structures or circuits for generating a magnetic field. In a preferred construction, each of the magnetic ends 40 are provided with a permanent rare earth magnet 45. As shown, the permanent magnets 45 are mounted at generally the same position in each of the magnetic ends 40. In the illustrated embodiment, the poles of the permanent magnets 45 are oriented so that the magnetic ends 40 are naturally attracted to one another. To this end, the permanent magnet 45 at the magnetic end 40 of one arm assembly is oriented so that its magnetic north pole is directly opposite and facing the magnetic south pole of the permanent magnet 45 at the magnetic end 40 of the other arm assembly.

A magnetic drive 50 is provided to magnetically induce rotation of the magnetic ends 40 about the respective rotation axes 25 and 30. In the illustrated embodiment, the magnetic drive 50 includes a magnetic element 55 and a mechanical or pneumatic drive 60. The drive 60 moves the magnetic element 55 between a first position in which the magnetic element 55 is interposed between the permanent magnets 45 at magnetic ends 40 of the arm assemblies 15 and 20 and a second position in which the magnetic element 55 is generally cleared from between the permanent magnets 45. The first position is illustrated in FIGS. 1A and 1B while the second position is illustrated in FIGS. 1C and 1D. As shown in FIGS. 1A and 1B, the magnetic poles of magnetic element 55 are oriented to repel the permanent magnets 45 away from the magnetic element 55 when the magnetic element 55 is driven to the first position. The forces generated by this magnetic repulsion cause magnetic ends 40 to rotate away from one another about their corresponding axes 25 and 30. In turn, holding ends 35 rotate toward one another to form the vessel holding pocket 43.

Magnetic drive 50 can be operated to form the vessel holding pocket 43 while an object that is to be held or transported by the apparatus 10 is located between holding ends 35. Alternatively, the object that is to be held or transported by the apparatus 10 may be deposited in the vessel holding pocket 43 after the holding ends 35 have been rotated toward one another and the pocket 43 has been formed.

As noted above, FIGS. 1C and 1D illustrate operation of the apparatus 10 when the drive 60 has driven the magnetic element 55 to the second position. In this position, the magnetic element 55 has been substantially cleared from between the permanent magnets 45 of the magnetic ends 40. Since the poles of the permanent magnets 45 are oriented to attract one another, the corresponding attractive forces draw the magnetic ends 40 toward one another thereby inducing a corresponding rotation of the holding ends 35 away from one another about axes 25 and 30. While in this position, an object that is to be held or manipulated by the apparatus 10 can be positioned between or removed from between the holding ends 35.

The construction and operation of the apparatus 10 shown in FIGS. 1A through 1D have been described with the magnetic poles of the permanent magnets 45 oriented in a naturally attractive state to bias the holding ends 35 to an open position. However, it will be recognized that the magnetic poles of the permanent magnets 45 can also be oriented in a naturally repulsive state to bias the holding ends 35 to the closed position shown in FIGS. 1A and 1B. In such instances, the poles of magnetic element 55 are oriented so that permanent magnets 45 are attracted toward the magnetic element 55 when the magnetic element 55 is between the permanent magnets 45.

In accordance with a still further variation of apparatus 10, drive 60 may be constructed to rotate magnetic element 55 to achieve the desired magnetic attractive and repulsive forces. In such instances, magnetic element 55 remains disposed between magnetic ends 40 and is rotated between first and second angular positions. In the first angular position, magnetic element 55 is rotated to an angle at which its magnetic poles repel magnetic ends 40 thereby causing the object holding ends 35 to move toward one another to a closed state. In the second angular position, magnetic element 55 is rotated to an angle at which its magnetic poles attract magnetic ends 40 thereby causing the object holding ends 35 to move away from one another to an opened state.

FIGS. 2A and 2B illustrate a variation on the embodiment of the apparatus 10 shown in FIGS. 1A through 1D. In the embodiment of FIGS. 2A and 2B, the magnetic element 55 and drive 60 have been replaced by an electromagnet 65 and a corresponding current control system 70. This embodiment can be operated in at least two different manners. First, the presence or absence of current provided by current control system 70 may be used to determine whether of the apparatus 10 is in an open or closed state. To this end, current control system 70 may be used to provide current through the electromagnet 65 to, for example, repel the permanent magnets 45 away from one another and direct holding ends 35 to a closed state. Holding ends 35 may then be directed to an open state by merely removing current from the electromagnet 65 and allowing the naturally attractive magnetic forces of permanent magnets 45 to draw the magnetic ends 40 toward one another. Second, the direction of the current provided by current control system 70 may be used to control the open or closed state of the apparatus 10. In this latter instance, the current control system 70 provides current through the electromagnet 65 in a first direction to repel the permanent magnets 45 away from one another and thereby drive the holding ends 35 toward one another to a closed state. The electrical current provided by current control system 70 would then be reversed to pole the permanent magnets 45 toward one another and thereby drive the holding ends 35 away from one another to an open state. In each instance, the operation of the current control system 70 may be placed under programmable computer control.

FIGS. 3A through 3E and FIGS. 4A through 4E illustrate another embodiment of apparatus for selectively holding and releasing an object in an analysis system that is constructed in accordance with the teachings of the present invention. The embodiment presented in these figures is specifically adapted to transport a microscope slide in the analysis unit. Generally stated, the apparatus, shown generally 75 of FIGS. 3A and 4A, includes a slide carriage assembly 80 that is mounted upon a carriage drive 85. Carriage drive 85 and carriage assembly 80 are connected with one another to allow carriage drive 85 to move carriage assembly 80 between a plurality of positions within the analysis unit. Carriage drive 85 may likewise be used to rotate carriage assembly 80 as it is driven between the various positions within the analysis unit. An assortment of carriage drives that can be modified for use in the illustrated embodiment are set forth in the '903 patent and '596 patent identified above. Other forms of carriage drives may likewise be employed.

The slide carriage assembly 80 includes a mounting frame 95 that serves as the principal support for the various components of the assembly 80. A lower portion of the mounting frame 95 is defined by a base element 100 that is used to connect the assembly 80 to the carriage drive 85. A pair of upstanding end pieces 105 extend from the base element 100 and terminate at a slide mounting bed 110. The mounting bed 110 may function as the principal support element for a microscope slide 115 that is to be transported or otherwise manipulated within the analysis system. Mounting bed 110 has a width that is less than the width of the microscope slide 115. Notches 117 extend inward toward a central line of the mounting bed 110 and terminate proximate the edges of the slide 115.

A pair of pivot rods 120 extend between end pieces 105. The pivot rods 120 are generally parallel with one another and are preferably suspended at the same elevation. Each pivot rod supports a corresponding arm assembly 125. Spacing elements 130 confine the longitudinal movement of each arm assembly 125 along the respective pivot rod 120. Preferably, the arm assemblies 125 are disposed at the same longitudinal position so that they are directly opposite one another on their respective rods 120.

Each arm assembly 125 includes a holding end 135 and a magnetic end 140 disposed on opposite sides of the corresponding pivot rod 120. The center of each pivot rod 120 thus defines a rotation axis for the corresponding arm assembly 125. Each pivot rod 120 extends through a centrally disposed aperture in a crossbeam 145 of the corresponding arm assembly 125.

The holding end 135 of each arm assembly 125 includes a pair of gripping arms 150 that proceed from the corresponding crossbeam 145. Each gripping arm 150 terminates at a groove 155. Notches 117 are aligned to receive the gripping arms 150. When the gripping arms 150 are in the holding state illustrated in FIGS. 3A through 3E, the inward surface of the grooves 155 limit horizontal motion of the slide 115 on the mounting bed 110 while the upper and lower surfaces of the grooves 155 limit vertical motion of the slide 115.

The magnetic end 140 of each arm assembly 125 includes a transverse beam 160 having a first end connected to the crossbeam 145 and a second end connected to a magnet housing 170. Each magnet housing 170 supports a corresponding permanent rare earth magnet 175.

In the illustrated embodiment, the magnets 175 are mounted so that they naturally bias the gripping arms 150 to the open state shown in FIGS. 3A through 3E. In this open state, the microscope slide 115 can be readily placed on or removed from mounting bed 110. To this end, the magnet 175 of one arm assembly 125 is mounted in its housing 170 so that its magnetic north pole directly faces the magnetic south pole of the magnet 175 mounted in the housing 170 of the other arm assembly 125.

A magnetic drive assembly, shown generally at 180, is employed to rotate the magnetic ends 140 about their respective pivot rods 120 and thereby rotate the gripping arms 150 between the open state shown in FIGS. 4A through 4E and the closed state shown in FIGS. 3A through 3E. The magnetic drive assembly 180 includes a drive motor 185, such as a linear stepper motor, that is mounted to one of the end elements 105. The motor 185 includes a drive rod 190 that is used to drive a magnetic piston assembly 195 that is likewise supported by at least one of the end elements 105. The magnetic piston assembly 195 includes a housing 200 that at least partially surrounds a reciprocating magnetic piston 205. As particularly shown in FIGS. 3D and 4D, magnetic piston 205 is comprised of a body portion 210 formed from a non-magnetic material and a permanent magnetic portion 215 that is supported by the body portion 210. The magnetic poles of the permanent magnetic portion 210 are oriented so that the permanent magnets 175 of the magnetic ends 140 are driven apart when the magnetic portion 210 is located between the permanent magnets 175.

Figure 4D:
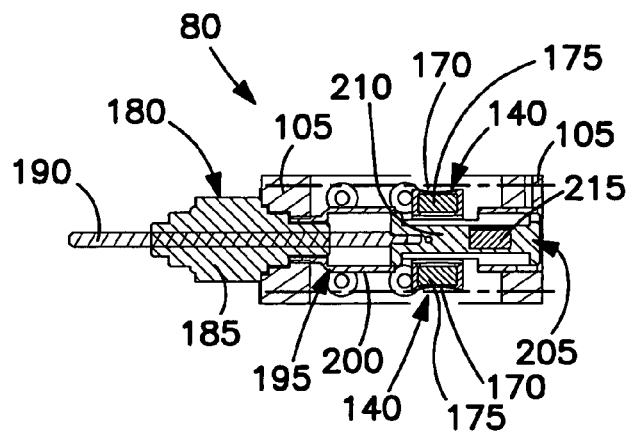
FIGS. 4A through 4E are schematic views of the second embodiment of the present invention in its open state.
Figure 4E:
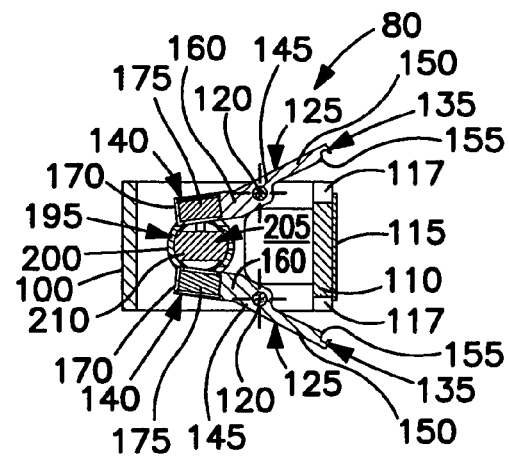
Figure 4A:
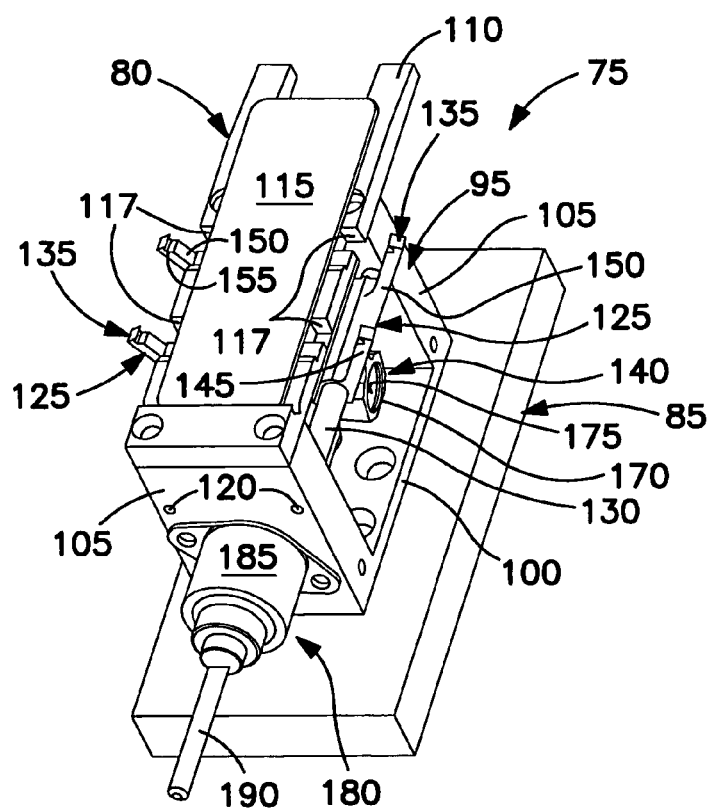
Figure 4B:
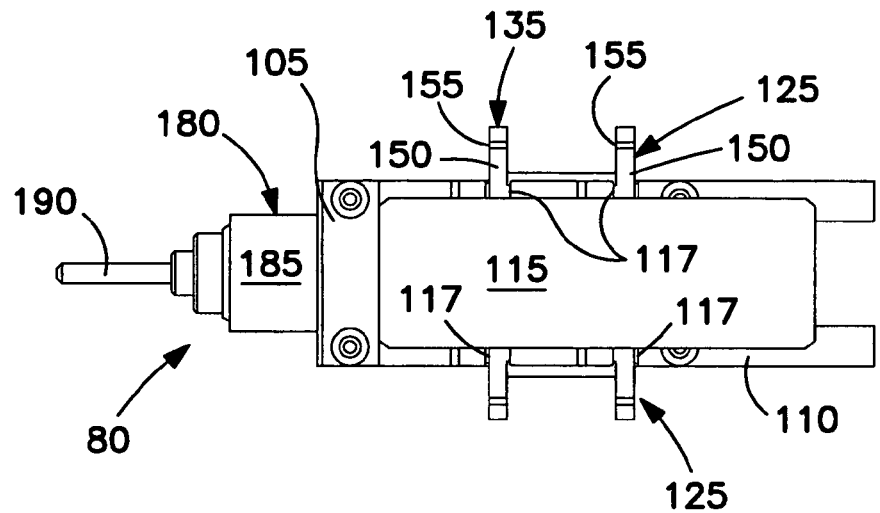
Figure 4C:
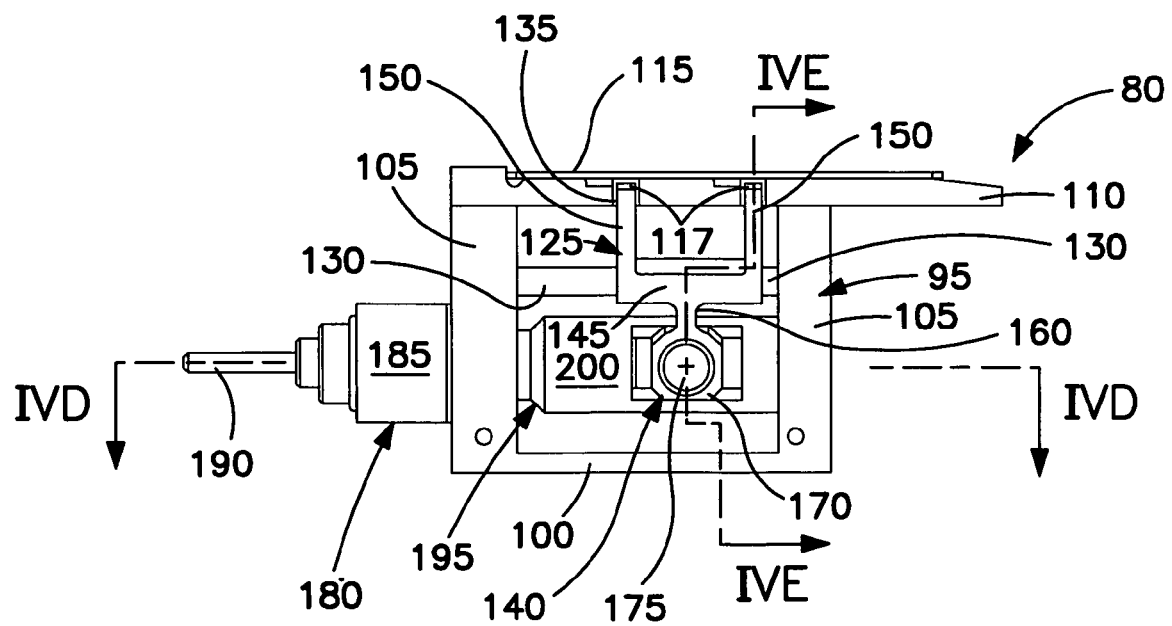

In operation, motor 185 and drive rod 190 first direct the magnetic piston 205 to the position shown in FIGS. 4D and 4E. With the magnetic piston 205 in this position, the permanent magnetic portion 210 is cleared from the area directly between the permanent magnets 175 of the arm assemblies 125 thereby causing the magnetic ends 140 to rotate toward one another. This rotational movement results in a corresponding rotation of the gripping arms 150 away from the mounting bed 110. In this open state, a microscope slide 115 may be readily placed upon or removed from the mounting bed 110. This condition is also illustrated in FIGS. 4A through 4C.

Figure 3E:
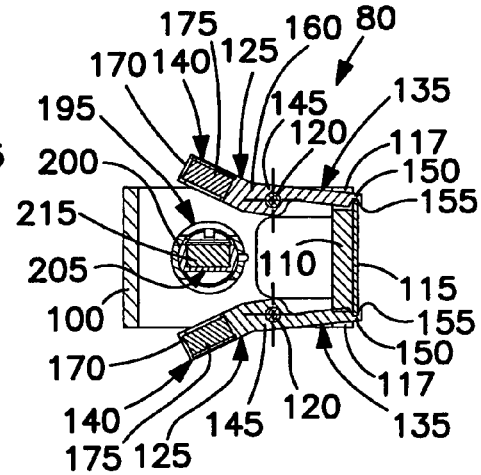
Figure 3A:
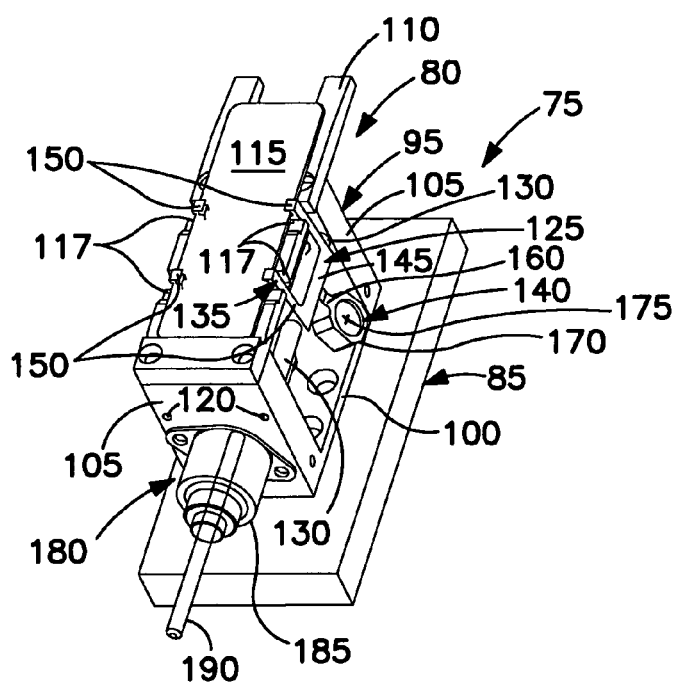
Figure 3B:
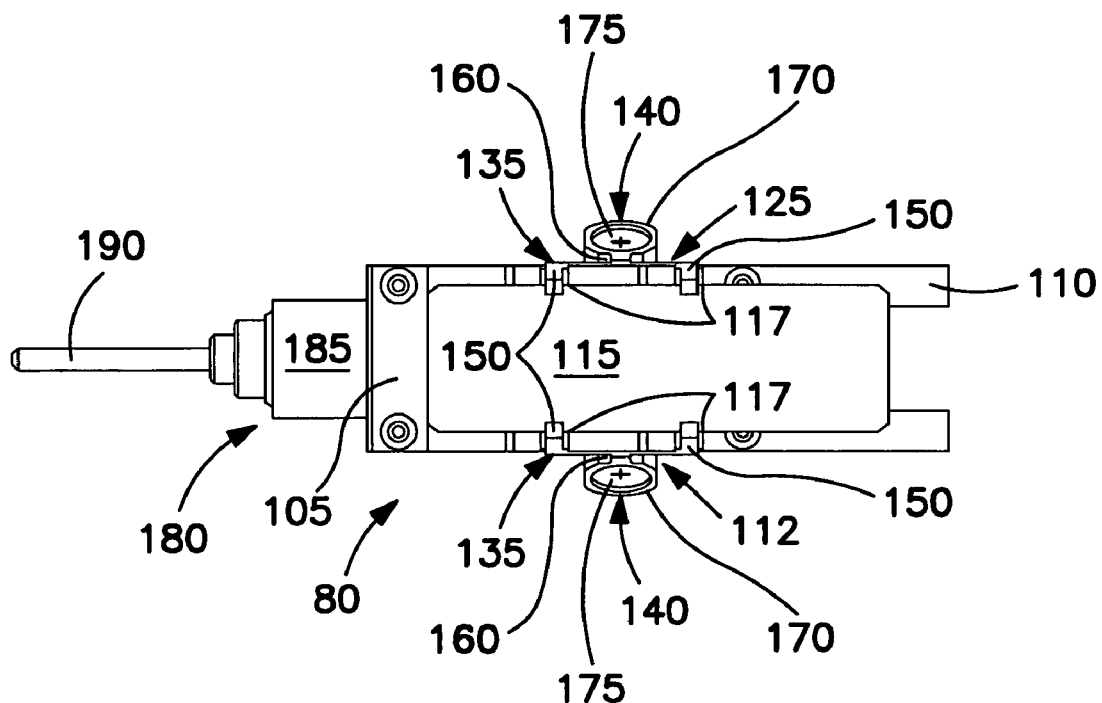
Figure 3C:
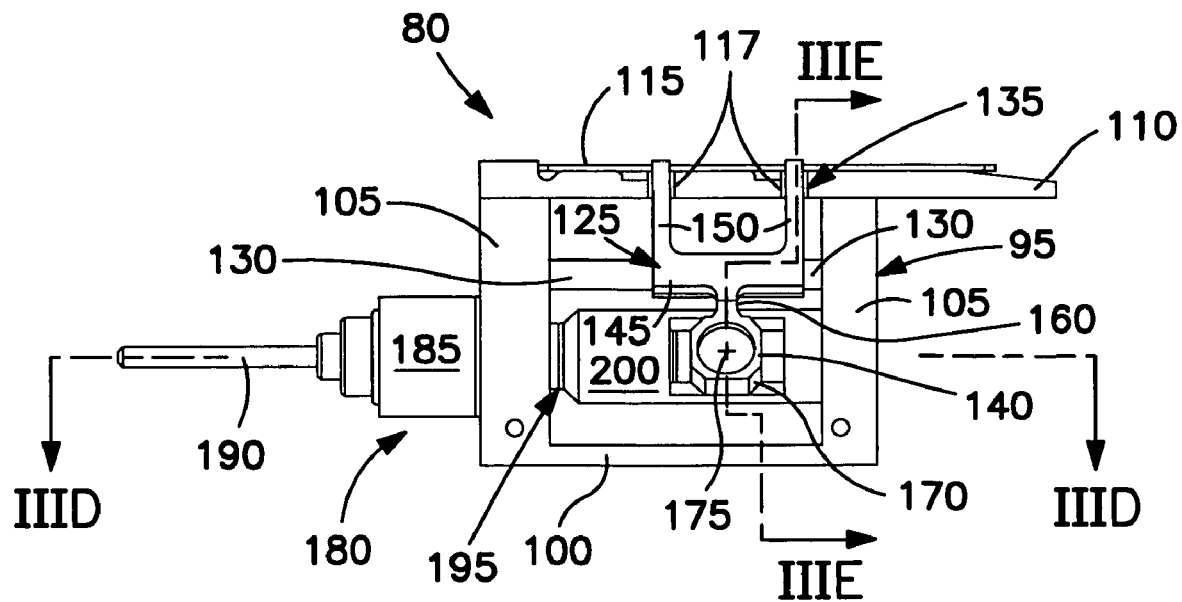

Once a microscope slide 115 has been placed upon the mounting bed 110, motor 185 and drive rod 190 direct the magnetic piston 205 to the position shown in FIGS. 3D and 3E. With the magnetic piston 205 in this position, the permanent magnetic portion 210 is disposed in the area directly between the permanent magnets 175 of the arm assemblies 125 thereby causing the magnetic ends 140 to rotate away from one another. This rotational movement results in a corresponding rotation of the gripping arms 150 toward the mounting bed 110. In this closed state, the microscope slide 115 is secured with the mounting bed 110 and the slide carriage drive 85 is free to move the slide carriage assembly 80. This condition is specifically illustrated in FIGS. 3A through 3C.

This second embodiment has been described with a given orientation of the various magnets within the apparatus. In this orientation, the gripping arms 150 are naturally biased to the open position and are driven to the closed position when the permanent magnetic portion 215 is moved to the area between the magnetic ends 140. However, it will be recognized that a natural bias of the gripping arms 150 to the closed position can be readily achieved by merely switching the orientation of the various magnetic poles in the apparatus 75. In this latter instance, the gripping arms 150 could be driven to the open position when the permanent magnetic portion 215 is moved to the area between the magnetic ends 140.

The first and second embodiments have also been shown with a linear stepper motor 185 that drives the magnetic portion 215 alternately between and away from magnets 175. It should also be recognized that motor 185 may be a rotary motor that rotates magnetic portion 215 while it is between magnets 175. In this manner, magnets 175 are driven toward and away from magnetic portion 215 based on the orientation of the magnetic poles of magnetic portion 215 with respect to the magnetic poles of magnets 175.

Figure 5A:
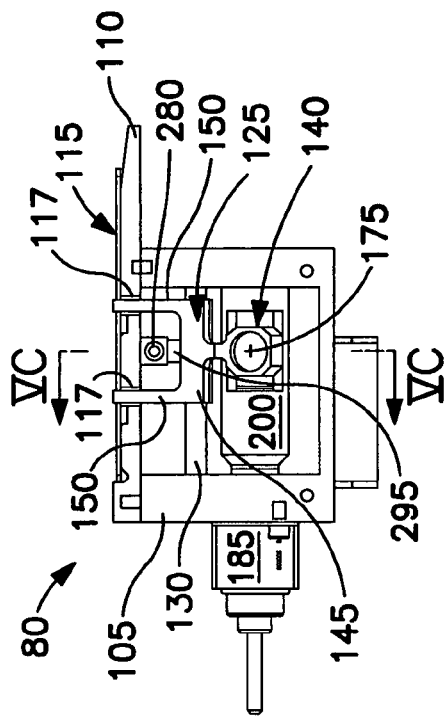
FIGS. 5A through 5C are schematic views of the second embodiment of the present invention in which an adjustment mechanism has been provided to set the spacing between the holding ends of the apparatus in its closed state.
Figure 5C:
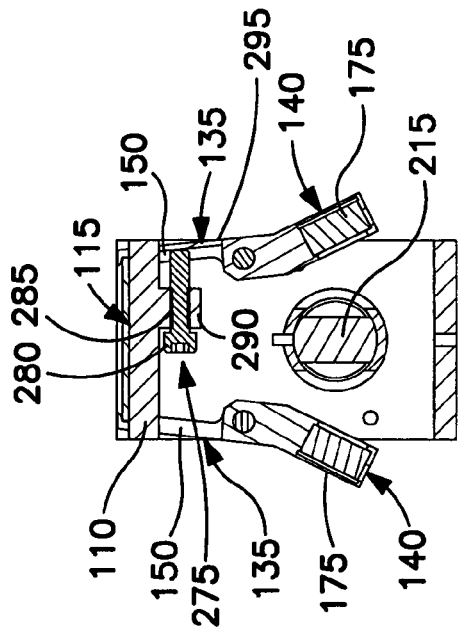
Figure 5B:
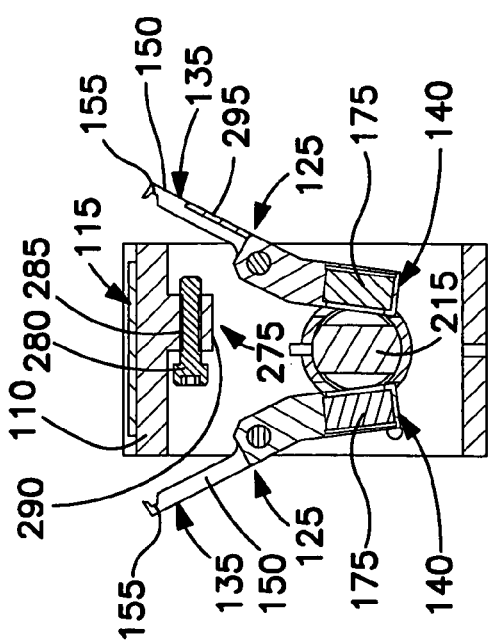

FIGS. 5A through 5C show the addition of a spacing adjustment mechanism 275 to the apparatus 80. Spacing adjustment mechanism 275 determines how far at least one of the gripping arms 150 is allowed to travel when the apparatus 80 is in its closed state. This travel distance, in turn, determines the lateral position that slide 115 will assume on the mounting bed 110 when the slide 115 is held between the gripping arms 150. Such adjustments allow the slide to be optimally positioned for various operations such as printing, smearing, etc.

In the illustrated embodiment, the spacing adjustment mechanism 275 includes an adjustment screw 280 that extends through a threaded aperture 285 in an extension block 290 at the underside of mounting bed 110. A stop member 295 extends from the crossbeam 145 and between the gripping arms 150 at a first side of the apparatus 80. The stop member 295 and the end of adjustment screw 280 are aligned to abut one another when the apparatus 80 is driven to the closed state illustrated in FIG. 5C. In this state, the travel of the gripping arms 150 associated with the stop member 295 is limited by the position of the end of the adjustment screw 280 thereby defining the position that slide 115 will assume on that side of the apparatus 80. Preferably, the gripping arms 115 on the opposite side of the apparatus 80 may move freely into the corresponding grooves 117 to urge the slide 115 to its proper position on the mounting bed 110.

Numerous modifications may be made to the foregoing system without departing from the basic teachings thereof. Although the present invention has been described in substantial detail with reference to one or more specific embodiments, those of skill in the art will recognize that changes may be made thereto without departing from the scope and spirit of the invention as set forth in the appended claims.

What is claimed is:

1. An apparatus for selectively holding and releasing an object in an analysis system, the apparatus comprising:
   a first arm mounted for rotation about a first axis, said first arm having an object holding end and a magnetic end disposed opposite one another about said first axis, wherein said first axis is intermediate to said object holding end and said magnetic end of said first arm;
   a second arm mounted for rotation about a second axis that is generally parallel to said first axis, said second arm having an object holding end and a magnetic end disposed opposite one another about said second axis, wherein said second axis is intermediate to said object holding end and said magnetic end of said second arm; and
   a magnetic drive adapted to magnetically induce rotation of said magnetic ends of said first and second arms about said first and second axes, respectively, wherein said magnetically induced rotation axially rotates said object holding ends.

2. An apparatus as claimed in claim 1 and further comprising a spacing adjustment mechanism disposed to limit movement of said first arm toward said second arm.

3. An apparatus as claimed in claim 1 wherein said magnetic ends of said first and second arms rotate between a first position in which said holding ends are distal to an object that is to be held and a second position in which said holding ends are proximate to said object.

4. An apparatus as claimed in claim 1 wherein said magnetic ends of said first and second members comprise permanent magnets.

5. An apparatus as claimed in claim 4 wherein said permanent magnets of said magnetic ends of said first and second arms are arranged so that they are magnetically attracted to one another to bias said magnetic portions toward one another.

6. An apparatus as claimed in claim 1 wherein said magnetic drive comprises:
   a permanent drive magnet; and
   a motor drive connected to said permanent drive magnet, said motor drive directing said permanent drive magnet between at least a first position in which said magnetic ends of said first and second arms rotate toward one another as a result of the position of said permanent drive magnet and a second position in which said magnetic ends of said first and second arms are rotated away from one another as a result of the position of said permanent drive magnet.

7. An apparatus as claimed in claim 6 wherein said motor drive comprises a linear stepper motor.

8. An apparatus as claimed in claim 6 wherein said permanent drive magnet is oriented to repel said magnetic ends of said first and second arms when said permanent drive magnet is disposed between said magnetic ends.

9. An apparatus as claimed in claim 1 wherein said magnetic drive comprises an electromagnet.

10. An apparatus as claimed in claim 9 and further comprising a control unit adapted to control electric current flow through said electromagnet.

11. An apparatus for selectively holding and releasing a carrier in an analysis unit, the carrier being adapted to hold a sample for analysis, the apparatus comprising:
    a mounting bed adapted to support the carrier;
    a first arm assembly having an arm portion at a first end thereof and a magnetic portion at a second end thereof, said first arm assembly being mounted for rotation about a first axis, wherein said first axis is intermediate to said first end and said second end of said first arm assembly;
    a second arm assembly having an arm portion at a first end thereof and a magnetic portion at a second end thereof, said second arm assembly being mounted for rotation about a second axis that is generally parallel to said first axis, and wherein said second axis is intermediate to said first end and said second end of said second arm assembly; and
    a magnetic drive adapted to magnetically induce rotation of said magnetic portions of said first and second arm assemblies toward and away from one another about said first and second axes thereby causing corresponding rotation of said arm portions of said first and second arm assemblies between a first position in which the carrier may be accepted upon said mounting bed and a second position in which the carrier may be secured upon said mounting bed with the assistance of said arm portions.

12. An apparatus as claimed in claim 11 and further comprising a spacing adjustment mechanism disposed to limit movement of said first arm assembly toward said second arm assembly when said first and second arm assemblies are in said second position.

13. An apparatus as claimed in claim 11 wherein said magnetic portions of said first and second arm assemblies comprise permanent magnets.

14. An apparatus as claimed in claim 13 wherein said permanent magnets of said magnetic portions of said first and second arm assemblies are arranged so that they are magnetically attracted to one another to bias said magnetic portions toward one another.

15. An apparatus as claimed in claim 11 wherein said magnetic drive comprises:
    a permanent drive magnet; and
    a motor drive connected to said permanent drive magnet, said motor drive directing said permanent drive magnet between at least a first position in which said magnetic portions of said first and second arm assemblies rotate toward one another as a result of the position of said permanent drive magnet and a second position in which said magnetic portions of said first and second arm assemblies are rotated away from one another as a result of the position of said permanent drive magnet.

16. An apparatus as claimed in claim 15 wherein said motor drive comprises a linear stepper motor.

17. An apparatus as claimed in claim 14 wherein said magnetic drive comprises:
   a permanent drive magnet; and
   a motor drive connected to said permanent drive magnet, said motor drive directing said permanent magnet between at least a first position in which said permanent drive magnet is disposed between said permanent magnets of said first and second arm assemblies and a second position in which said permanent drive magnet is moved away from between said permanent magnets of said first and second arm assemblies.

18. An apparatus as claimed in claim 17 wherein said motor drive comprises a linear stepper motor.

19. An apparatus as claimed in claim 17 wherein said permanent drive magnet is oriented to repel said permanent magnets of said first and second arm assemblies when said permanent drive magnet is disposed between said magnetic portions.

20. An apparatus as claimed in claim 14 wherein said magnetic drive comprises an electromagnet.

21. An apparatus as claimed in claim 20 and further comprising a control unit adapted to control electric current flow through said electromagnet.

22. An apparatus for transporting a slide in an analysis unit, the apparatus comprising:
   a slide carriage assembly comprising:
      a mounting bed adapted to support the slide,
      a first arm assembly having an arm portion at a first end thereof and a magnetic portion at a second end thereof, said first arm assembly being mounted for rotation about a first axis, wherein said first axis is intermediate to said first end and said second end of said first arm assembly,
      a second arm assembly having an arm portion at a first end thereof and a magnetic portion at a second end thereof, said second arm assembly being mounted for rotation about a second axis that is generally parallel to said first axis, and wherein said second axis is intermediate to said first end and said second end of said second arm assembly,
      a magnetic drive adapted to magnetically induce rotation of said magnetic portions of said first and second arm assemblies toward and away from one another about said first and second axes thereby causing corresponding rotation of said arm portions of said first and second arm assemblies between a first position in the slide may be accepted upon said mounting bed and a second position in which the slide may be secured upon said mounting bed with the assistance of said arm portions; and
   a carriage drive connected to move said slide carriage assembly between a plurality of positions within the analysis unit.

23. An apparatus as claimed in claim 22 and further comprising a spacing adjustment mechanism disposed to limit movement of said first arm assembly toward said second arm assembly when said first and second arm assemblies are in said second position.

24. An apparatus as claimed in claim 22 wherein said magnetic portions of said first and second arm assemblies comprise permanent magnets.

25. An apparatus as claimed in claim 24 wherein said permanent magnets of said magnetic portions of said first and second arm assemblies are arranged so that they are magnetically attracted to one another to bias said magnetic portions toward one another.

26. An apparatus as claimed in claim 22 wherein said magnetic drive comprises:
   a permanent drive magnet; and
   a motor drive connected to said permanent drive magnet, said motor drive directing said permanent drive magnet between at least a first position in which said magnetic portions of said first and second arm assemblies rotate toward one another as a result of the position of said permanent drive magnet and a second position in which said magnetic portions of said first and second arm assemblies are rotated away from one another as a result of the position of said permanent drive magnet.

27. An apparatus as claimed in claim 26 wherein said motor drive comprises a linear stepper motor.

28. An apparatus as claimed in claim 25 wherein said magnetic drive comprises:
   a permanent drive magnet; and
   a motor drive connected to said permanent drive magnet, said motor drive directing said permanent magnet between at least a first position in which said permanent drive magnet is disposed between said permanent magnets of said first and second arm assemblies and a second position in which said permanent drive magnet is moved away from between said permanent magnets of said first and second arm assemblies.

29. An apparatus as claimed in claim 28 wherein said motor drive comprises a linear stepper motor.

30. An apparatus as claimed in claim 28 wherein said permanent drive magnet is oriented to repel said permanent magnets of said first and second arm assemblies when said permanent drive magnet is disposed between said permanent magnets.

31. An apparatus as claimed in claim 25 wherein said magnetic drive comprises an electromagnet.

32. An apparatus as claimed in claim 31 and further comprising a control unit adapted to control electric current flow through said electromagnet.

33. An apparatus for selectively holding and releasing a carrier during transport in an analysis unit, the apparatus comprising:
   a mounting bed adapted to contact the carrier;
   a first clamp member mounted for rotation about a first axis, said first clamp member having a carrier gripping end and a magnetic end disposed on opposite sides of said first axis;
   a second clamp member mounted for rotation about a second axis that is generally parallel to said first axis, said second clamp member having a carrier gripping end and a magnetic end disposed on opposite sides of said second axis; and
   a magnetic drive adapted to magnetically induce rotation of said magnetic ends of said first and second clamp members about said first and second axes, respectively, to thereby cause the axial rotation of the clamp members to secure the carrier to said mounting bed.

34. An apparatus as claimed in claim 33 wherein said magnetic ends of said first and second clamp members rotate between a first position in which said gripping ends are distal said mounting bed and a second position in which said gripping ends are proximate said mounting bed.

35. An apparatus as claimed in claim 34 wherein said gripping ends are adapted to clamp the carrier against said mounting bed in said second position.

36. An apparatus as claimed in claim 33 wherein said magnetic ends of said first and second clamp members comprise permanent magnets.

37. An apparatus as claimed in claim 36 wherein said permanent magnets of said magnetic ends of said first and second clamp members are arranged so that they are magnetically attracted to one another to bias said magnetic portions toward one another.

38. An apparatus as claimed in claim 33 wherein said magnetic drive comprises:
   a permanent drive magnet; and
   a motor drive connected to said permanent drive magnet, said motor drive directing said permanent drive magnet between at least a first position in which said magnetic ends of said first and second clamp members rotate toward one another as a result of the position of said permanent drive magnet and a second position in which said magnetic ends of said first and second clamp members are rotated away from one another as a result of the position of said permanent drive magnet.

39. An apparatus as claimed in claim 38 wherein said motor drive comprises a linear stepper motor.

40. An apparatus as claimed in claim 38 wherein said permanent drive magnet is oriented to repel said magnetic ends of said first and second clamp members when said permanent drive magnet is disposed between said magnetic ends.

41. An apparatus as claimed in claim 33 wherein said magnetic drive comprises an electromagnet.

42. An apparatus as claimed in claim 41 and further comprising a control unit adapted to control electric current flow through said electromagnet.

43. An analysis system, comprising:
   a slide adapted to receive a sample to be analyzed;
   a first arm mounted for rotation about a first axis, said first arm having a slide clamping portion and a magnetic portion, wherein said first axis is intermediate to said slide clamping portion and said magnetic portion of said first arm;
   a second arm mounted for rotation about a second axis, said second arm having a slide clamping portion and a magnetic portion, wherein said second axis is intermediate to said slide clamping portion and said magnetic portion of said second arm;
   a mounting bed adapted to support said slide, said mounting bed disposed intermediate to said first arm and said second arm; and
   a magnetic drive adapted to magnetically induce rotation of the magnetic portions of said first and second arms about the first and second axes, respectively, wherein said magnetically induced rotation axially rotates said object holding ends.

44. An analysis system as claimed in claim 43, wherein said first and second arms rotate between a first position in which the slide clamping portions clamp said slide to said mounting bed and a second position in which said slide is not clamped.

45. An analysis system as claimed in claim 43, further comprising a space adjustment member disposed perpendicular to the first and second axes.

46. An analysis system as claimed in claim 43, wherein the slide clamping portions are disposed at a first end of said first and second arms.

47. An analysis system as claimed in claim 46, wherein the magnetic portions are disposed at a second end of said first and second arms.

48. An analysis system as claimed in claim 43, wherein the magnetic portions comprise permanent magnets.

* * * * *

UNITED STATES PATENT AND TRADEMARK OFFICE
CERTIFICATE OF CORRECTION

PATENT NO. : 7,597,845 B2
APPLICATION NO. : 10/923975
DATED : October 6, 2009
INVENTOR(S) : Thomas E. Domack It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1386 days.

Signed and Sealed this

Twenty-eighth Day of September, 2010

David J. Kappos
*Director of the United States Patent and Trademark Office*